United States Patent [19]

Pottberg

[11] Plant 5,214

[45] Apr. 3, 1984

[54] CUPHEA PLANT TABLE TOP BONSAI

[76] Inventor: Clifton F. Pottberg, P.O. Box 5130, Hudson, Fla. 33567

[21] Appl. No.: 425,932

[22] Filed: Sep. 28, 1982

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Duckworth, Allen, Dyer & Pettis

[57] ABSTRACT

A new seedling of *Cuphea hyssopifolia* characterized by a dwarf size, internodal dwarfing, a spreading growth form and profuse, substantially constant blooming.

2 Drawing Figures

BACKGROUND OF THE INVENTION

The invention described herein is a new and distinct variety of Cuphea plant discovered by me at Sparks, Md. The new variety was obtained as a seedling from *Cuphea hyssopifolia.* The new variety was selected by me as a single variant plant from a crop of the parent variety being grown under my direction and control.

The seedling was noted and selected due to its compact size and shape. The seedling is distinct from the parent variety and from all other Cuphea varieties of which I am aware in having markedly dwarfed internodal spacing, a spreading growth habit, and an overall height of no more than about 30 cm. The dwarf size and dense, spreading shape of this new variety results in a commercially valuable plant that is particularly suited for interior decoration. The new variety is also somewhat more profuse in blooming than its parent.

Asexual reproduction of my new Cuphea variety was performed by me by cuttings at Sparks, Md., and at Hudson, Fla., with its distinct and characteristic traits stable and perpetuated through successive propagations.

As a varietal name for my new seedling, I have chosen Table Top Bonsai.

BRIEF DESCRIPTION OF THE DRAWINGS

The accompanying photographs show typical specimen plants of my new variety in color as nearly true as it is reasonably possible to make the same in color photographs of this character.

DETAILED DESCRIPTION OF THE PLANT

The following is a detailed description of my new Cuphea variety, Table Top Bonsai—Heather, as based on observation of specimen plants grown in Hudson, Fla. Color terminology is in accordance with the Universal Color Language as presented in F. B. Smithe, Naturalist's Color Guide and Naturalist's Color Guide Supplement (1974–75), published by the American Museum of Natural History, New York, N.Y. Color names and numbers refer to basic colors which may then be modified by terms such as "dark" or "light."

Parentage: Seedling of *Cuphea hyssopifolia.*

Propagation: Holds its distinguishing dwarf size and internodal dwarfing characteristics through successive propagation by cuttings.

PLANT

Habit: Small, compact shrub.

Growth: Compact shrub to 30 cm in height; main branches numerous, fine, spreading.

STEM

Terete, initially less than 1 mm in diameter, increasing with age and branching from only one of each pair of leaf axils, flowering from the other. Stem color dark carmine (#8) dulled with green in color, covered with simple, short, curved, whitish hairs, with occasional larger reddish (dull carmine) hairs.

LEAVES

Placement: Opposite, pairs 4–5 mm apart.

Shape: Oblanceolate, tip acute, margin entire, somewhat revolute.

Size: 12–14 mm long; 4–4.5 mm wide at widest point; petiole about 0.5 mm long.

Texture: Gloss above; dull below.

Color of adaxial surface of blade: Dark apple green (#61), with irregular splotches of dark carmine dulled with green.

Color of abaxial surface of blade: Pale apple green (#61), with veins green to dark carmine.

FLOWERS

Placement: Solitary, in the axil of only one of each pair of leaves, pedicel adnate to the stem, separating just below the next pair of leaves. Flowering continuous and profuse under good growing conditions.

Form: Of the usual form for the species.

Color: Purple (#1).

What is claimed is:

1. A new and distinct variety of Cuphea plant substantially as herein described, characterized particularly as to novelty by its compact size, internodal dwarfing, and spreading growth form.

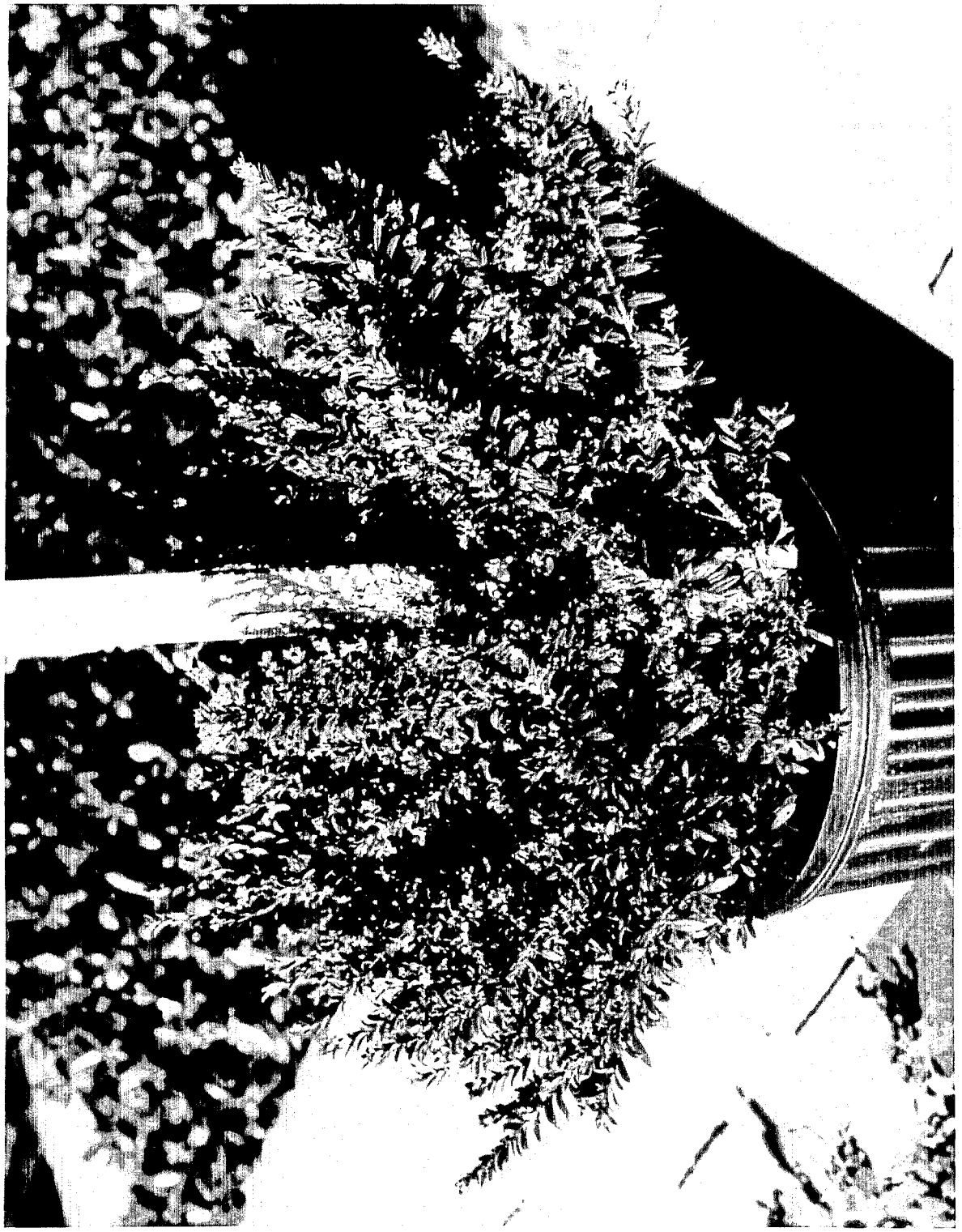

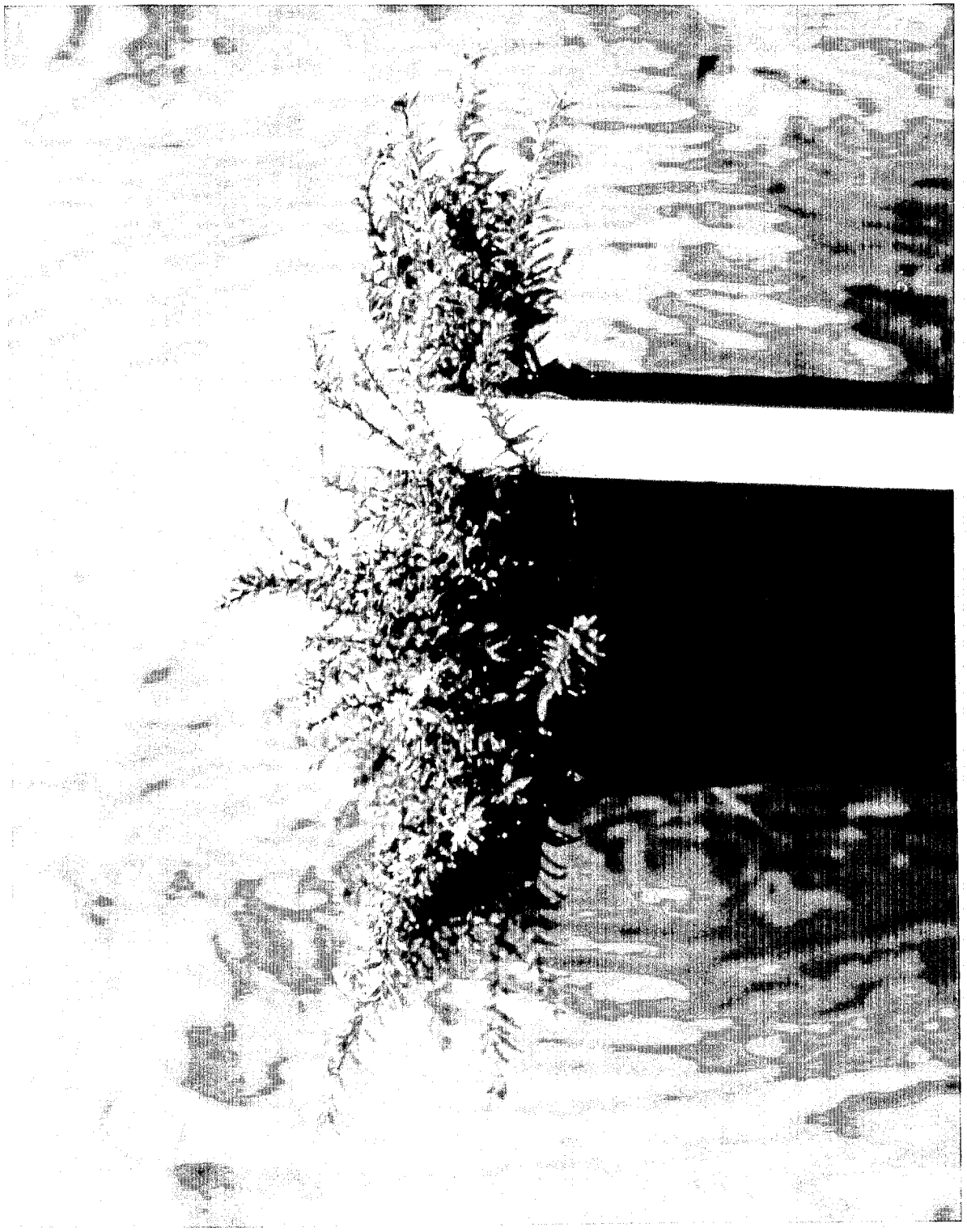

* * * * *